United States Patent [19]

Buford, III et al.

[11] Patent Number: 5,405,398
[45] Date of Patent: Apr. 11, 1995

[54] PROSTHETIC KNEE WITH POSTERIOR STABILIZED FEMORAL COMPONENT

[75] Inventors: Thomas B. Buford, III, Austin; Charles H. Perrone, Jr., Manchaca; Jeffery C. Higgins, Austin, all of Tex.

[73] Assignee: Intermedics Orthopedics, Inc., Austin, Tex.

[21] Appl. No.: 114,661

[22] Filed: Aug. 30, 1993

[51] Int. Cl.⁶ .............................................. A61F 2/38
[52] U.S. Cl. .................................... 623/20; 623/21; 403/154; 403/156; 403/163; 411/999
[58] Field of Search ............... 623/20, 21; 403/118, 403/152, 154–156, 163, DIG. 7; 411/22, 26, 147, 151, 159, 353, 337, 396–397, 999

[56] References Cited

U.S. PATENT DOCUMENTS

| 3,503,431 | 3/1970 | Villo et al. ................. 411/999 X |
| 3,638,980 | 2/1972 | Kleinhenn ................. 411/999 X |
| 3,812,756 | 5/1974 | Wenger ..................... 411/999 X |
| 3,899,796 | 8/1975 | Bahler et al. .................... 623/21 |
| 4,262,368 | 4/1981 | Lacey ............................ 623/20 |
| 4,470,735 | 9/1984 | Salisbury ...................... 411/353 |
| 4,747,738 | 5/1988 | Duran .......................... 411/353 |
| 4,795,468 | 1/1989 | Hodorek et al. ............... 623/18 |
| 5,011,496 | 4/1991 | Forte et al. ................... 623/20 |
| 5,156,626 | 10/1992 | Broderick et al. .............. 623/22 |

FOREIGN PATENT DOCUMENTS

| 0278184 | 8/1988 | European Pat. Off. ........... 623/21 |
| 2385934 | 10/1978 | France ........................ 411/147 |

*Primary Examiner*—David H. Willse
*Attorney, Agent, or Firm*—John R. Merkling

[57] ABSTRACT

A posterior stabilized knee prosthesis with removable pin in the femoral component. The removable pin has a tapered split ring lock which prevents the pin from backing out. A split ring is provided on the pin which rides in a groove on the pin. When the pin is properly seated, the split ring engages a corresponding groove within the femoral prosthesis, locking the pin in place. Chamfers are provided on both the front and back of the split ring so that the split ring will compress as the pin is being screwed into the femoral component and also so that the pin can be removed if necessary.

16 Claims, 3 Drawing Sheets

PROSTHETIC KNEE WITH POSTERIOR STABILIZED FEMORAL COMPONENT

BACKGROUND OF THE INVENTION

Our invention is in the general area of orthopedic prostheses, particularly, artificial knees. Specifically, our invention relates to a femoral component of an artificial knee prosthesis which can be used with or without a posterior stabilized feature.

The two largest and longest bones of the human body, femur and the tibia, meet at a person's knee. The tibia is situated at the front and inner side of the lower leg. It is prismoid in form, and expanded above where it enters into the knee joint. At the top of the tibia are two smooth compartments or surfaces which articulate with the condyles of the femur. Posteriorly, the condyles and compartments are separated from each other by a shallow depression for the attachment of ligaments. Because the knee has great mobility in flexion, it relies on a set of ligaments to constrain its motion when bent. These include the medial and lateral collateral ligaments and the posterior and anterior cruciate ligaments.

Because of wear and tear or disease, the articulating surfaces of the knee may degrade. To treat certain pathologies, it has become common to surgically remove either the condyles or the compartments or both and replace these structures with prosthetic implants. To preserve the ligaments around the knee, it is desirable to remove as little of the bone structure as possible. However, conditions may dictate that a larger amount of the bone structure be removed in the first instance, or the degradation of bone or ligaments may continue after the initial implants, requiring a revision or second operation wherein more bone is removed and a more robust prosthesis is installed. In these situations, the attachments sites of the constraining ligaments may also of necessity be removed. In these situations, the constraining action of the ligaments must be replaced by another mechanism.

Such a mechanism is known in the art as a posterior stabilized prosthetic knee. These structures typically have an eminence in the center of an articulating surface of the tibial component which mates with pronounced cross member in the femoral component. They are constrained from tibial posterior translation by the posterior wall of this tibial prominence engaging femoral cross member. Such a prosthesis is known from U.S. Pat. No. 4,213,299 to Insall.

When a revision operation is necessary, it is sometimes desirable to add a posterior stabilized feature because the posterior cruciate ligament has continued to degenerate, although the femoral surfaces have not. It has been suggested by Hofmann, U.S. Pat. No. 5,116,375, that a removable stabilizing rod or pin should be provided in the femoral component which can be added during the revision operation without removing the femoral prosthesis.

SUMMARY OF OUR INVENTION

We have invented an improvement on the posterior stabilized knee prosthesis with removable pin in the femoral component. In particular, we have designed a removable pin with a tapered split ring lock which prevents the pin from backing out.

The removable pin is screwed into the femoral component through the medial condyle of that component. A split ring is provided on the pin which rides in a groove on the pin. When the pin is properly seated, the split ring engages a corresponding groove within the femoral prosthesis, locking the pin in place. Chamfers are provided on both the front and back of the split ring so that the split ring will compress as the pin is being screwed into the femoral component and also so that the pin can be removed if necessary.

We have described our invention with particular reference to a posterior stabilized femoral knee prosthesis, but our invention could also be used in other prosthetic applications where it is desired to attach a pin or shaft to another part, particularly by a threaded attachment, and to provide a means to resist unintentional disassembly of the shaft and part.

With the foregoing in mind, it is an object of our invention to provide a knee joint prosthesis with an optional posterior stabilized feature and removable pin in a femoral component.

It is further an object of our invention to provide a selectively attachable pin or shaft in a prosthesis which resists removal in use.

It is a further object of our invention to provide such a pin which, although resisting removal, can nevertheless be removed under proper conditions.

These and other objects and features of our invention will be apparent from the following detailed description taken to reference to the accompanying drawings.

DETAILED DESCRIPTION OF OUR PREFERRED EMBODIMENT

Figure 1:
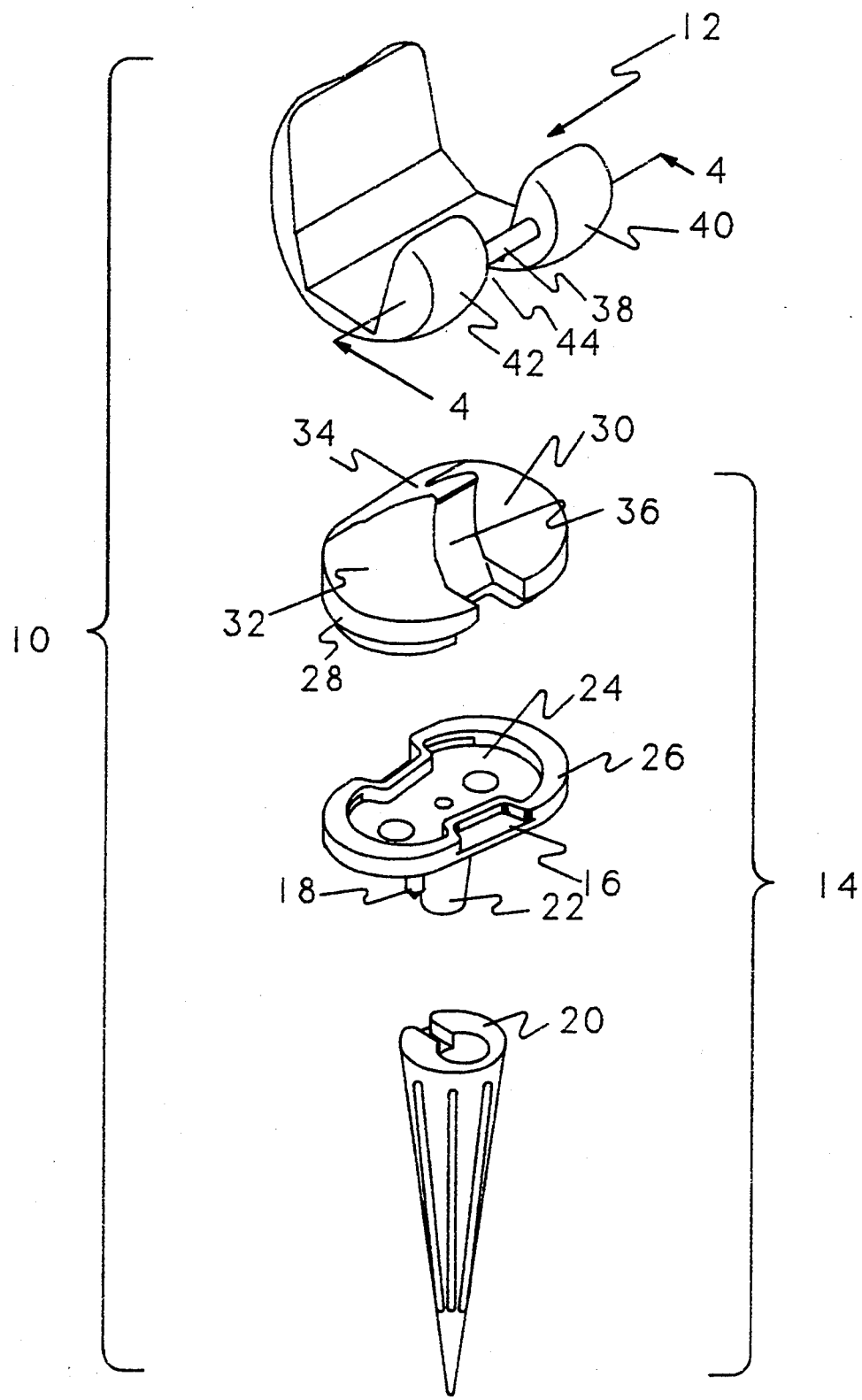
FIG. 1 is an exploded prospective view of a prosthetic knee according to our present invention.

We will now describe our preferred embodiment of our invention by reference to the accompanying drawings. In the drawings, like numerals will refer to like parts in each drawing. FIG. 1 shows an exploded prospective view of a prosthetic knee 10. The knee 10 comprises a femoral component 12 and tibial component 14. The tibial component comprises a base plate 16 with fixation means for attaching the base plate 16 to the resected upper surface of a tibia. In the illustrated embodiment, the fixation means comprise pins 18 and a removable shaft 20 for insertion into the medullary canal of the tibia. The shaft 20 is releasably mounted on a post 22. Other features, known in the art, may be provided, such as porous surfaces, or fixation screws. The base plate 16 has a superior cavity 24 surrounded by a lip 26 for receiving an insert 28 of ultra high molecular weight polyethylene. The insert 28 has medial and lateral articulating surfaces 30, 32 respectively. The articulating surfaces 30, 32 are separated by a central stabilizing eminence 34. If it is desirable to use the prosthesis without a posterior stabilizing feature, an insert without the stabilizing eminence would be employed, as is known in the art. This is simply a matter of substituting one insert for another. The stabilizing eminence 34 has a posterior surface 36 for engaging a pin 38 in the femoral component.

As will be more particularly explained below, the pin 38 is removable and may be inserted when a posterior stabilizing feature is desired but otherwise may be omitted. The femoral component 12 comprises medial and lateral condyle parts 40, 42, respectively, which articulate with the articulating surfaces 30, 32 of the insert 28. Between the condyle parts 40, 42 a central groove 44 is provided. This groove 44 is deep so that it may receive the stabilizing eminence 34 in sliding relationship. This improves the stability of the knee, particularly in the absence of the natural ligaments which otherwise constrain the motion of the knee. Moreover, as the knee is bent, the posterior surface 36 of the post 34 will contact the pin 38 causing the femoral and tibial components to be in both rolling and sliding contact with respect to each other, thereby reproducing the natural motion of the healthy knee.

Figure 2:
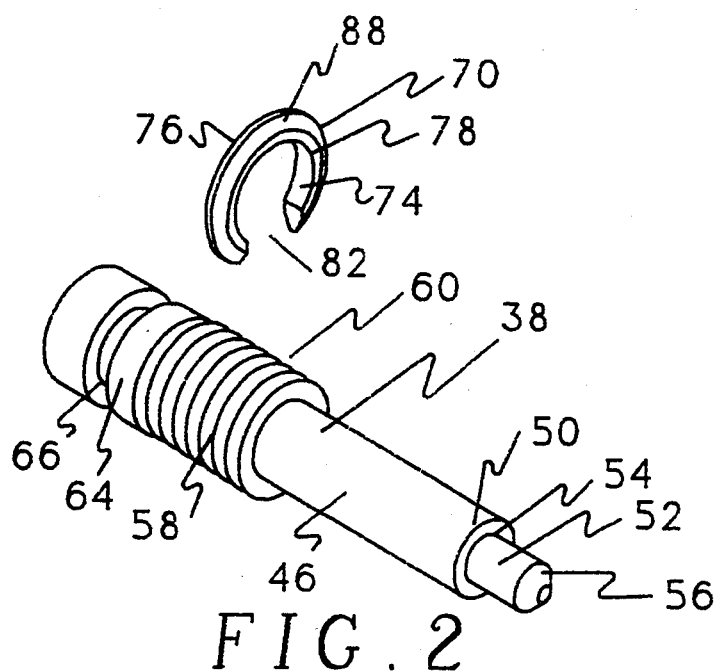
FIG. 2 is a prospective view of a pin and split ring according to our invention.
Figure 3:
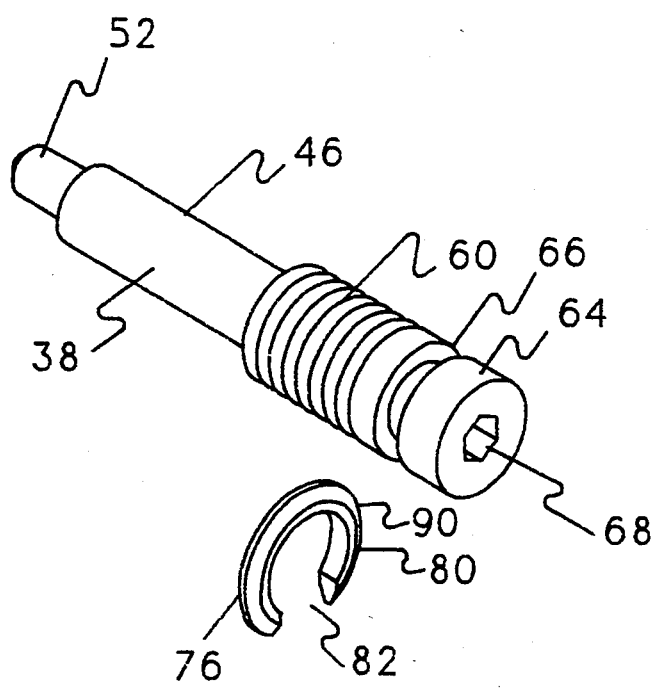
FIG. 3 is a reverse prospective view of the pin and split ring of FIG. 2.

We will now describe the removable pin 38 in greater detail by reference to FIGS. 2 and 3.

Figure 4:
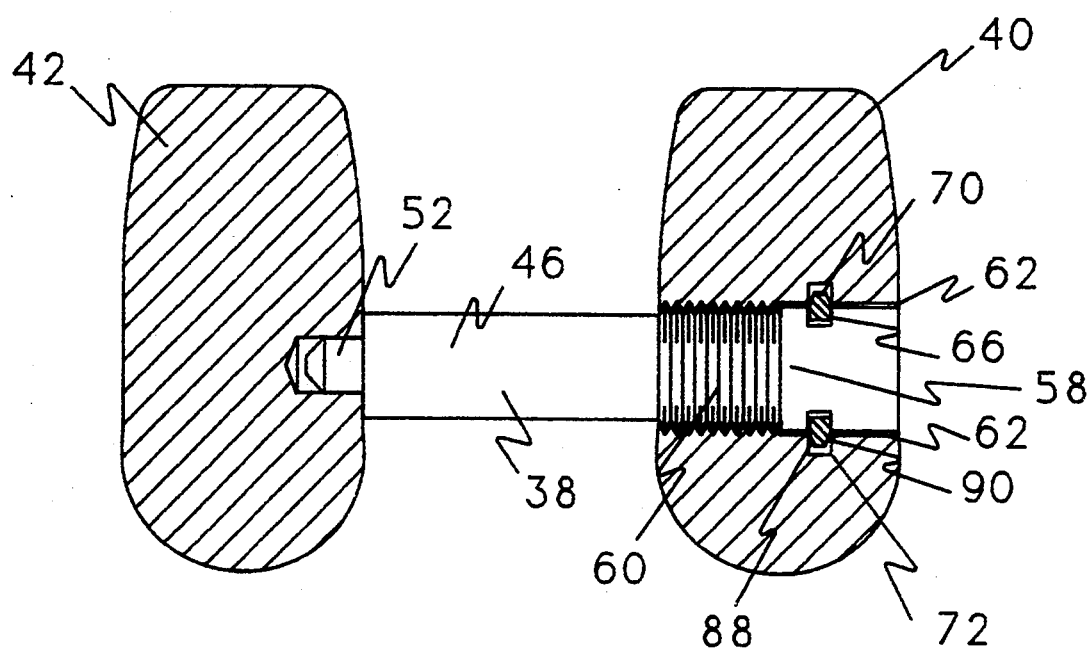
FIG. 4 is a partial through section of a femoral component shown in FIG. 1 taken along line 4—4.

The pin 38 comprises a shaft 46 with a surface 48 which is exposed between the condyle parts 40, 42 when the pin is assembled in the femoral component. At a lateral end 50 of the pin, a reduced diameter post 52 is provided, forming a shoulder 54. The post 52 is tapered or pointed at its end 56. When the pin 38 is inserted into the femoral component 12, the post 52 engages a blind bore in the lateral condyle, for example, condyle part 42. The shoulder 54 seats against the outer surface of the condyle part 42. The taper at the end 56 of the post makes assembly easier by guiding the post into the bore. Near a medial end 58 of the pin threads 60 are provided for securing the pin in a partially threaded shaft 62 (FIG. 4) in a condyle part, such as part 40. Between the medial end 58 and the threads 60, the pin has an enlarged shaft 64 with a circumferential groove 66. A wrench engaging feature 68 is also provided so that the pin may be screwed into the component 12. In the illustrated embodiment, a hexagonal bore is shown.

A split ring 70 rides in the groove 66. This split ring prevents the inadvertent disassembly of the component 12 by engaging a corresponding circumferential groove 72 within the condyle part 40. The split ring has an inner circumferential surface 74 adjacent the pin and an outer circumferential surface 76 which, when installed, will be adjacent the groove in the condyle part. First and second walls 78, 80 join the inner and outer surfaces 74, 76. A gap 82 permits the split ring to be assembled onto the pin in a known manner.

Between the first wall 78 and the external circumferential surface 76 there is a chamfer 88. As the pin is inserted into the component 12, this chamfer 88 will contact the opening of the partially threaded bore in the condyle part 40. As this occurs there is a noticeable resistance to turning, but the chamfer is so chosen as to compress the split ring within the groove 66, allowing the pin to be further threaded into the bore 62. When the pin is fully inserted, and the shoulder 54 contacts the other condyle part 42, the split ring will be adjacent the interior corresponding groove 72 and will expand into the groove, thereby providing a locking feature which resists the disassembly of the pin from the component 12.

Because it may also be desirable to disassemble the component 12, a second chamfer 90 is provided between the second wall 80 and the external circumferential surface 76. If a surgeon desires to unscrew the pin, the action of the second chamfer 90 against the groove 72 will collapse the ring into the groove 66, allowing the pin to be withdrawn. However, the force necessary to initiate withdrawal of the pin is significantly greater than the torque generated by in vivo articulation. Our invention, therefore, provides a pin with a positive locking feature, which can nevertheless be disassembled without additional tools, should disassembly be desired.

Our invention may be embodied in other forms without departing from the spirit or teaching thereof. The foregoing description is therefore, to be considered illustrative and the scope of our invention is to defined by the following claims. All changes which would come within the meaning of equivalency of the claims are intended to be encompassed therein.

We claim as our invention:

1. A femoral knee prosthesis for use selectively as a cruciate retaining prosthesis or a posterior stabilized prosthesis, said prosthesis having medial and lateral condyle parts, a transverse shaft adapted to be selectively installed between the condyle parts, said parts having a bore therein for selectively receiving said transverse shaft, said bore having securing means in at least one of said parts for securing said shaft in said bore,
   a circumferential groove on said shaft,
   a corresponding groove in said bore, which corresponding groove will lie adjacent said groove on said shaft when said shaft is properly inserted in said bore,
   a split ring carried in one of said grooves, said ring being capable of being displaced substantially entirely within said one of said grooves but normally extending radially out of said one of said grooves, said ring having two opposed chamfers, said chamfers being normally exposed out of said one of said grooves,
   whereby said split ring is displaced within said one of said grooves as said shaft is inserted into said bore until the other of said grooves is adjacent said one of said grooves and whereby said split ring is also displaced within said one of said grooves to withdraw said shaft from said bore.

2. The prosthesis according to claim 1 wherein said securing means comprise a threaded portion on said shaft and a threaded section in said bore.

3. The prosthesis according to claim 2 wherein the threaded portion on said shaft is adjacent said circumferential groove and wherein said threaded section in said bore is adjacent said corresponding groove.

4. The prosthesis according to claim 3 wherein said bore is stopped in one of said condyle parts and said threaded section and said corresponding groove lie in the other of said condyle parts.

5. The prosthesis according to claim 4 wherein said shaft further comprises a post on a distal end thereof for insertion into said condyle part having said stopped bore.

6. The prosthesis according to claim 5 wherein said shaft further comprises wrench engaging means on a proximal end thereof.

7. The prosthesis according to claim 1 wherein said split ring is carried in said circumferential groove, said ring being capable of being compressibly received substantially entirely within said circumferential groove but normally extending radially outwardly from said circumferential groove.

8. The prosthesis according to claim 7 wherein said securing means comprise a threaded portion on said shaft and a threaded section in said bore.

9. The prosthesis according to claim 8 wherein the threaded portion on said shaft is adjacent said circumferential groove and wherein said threaded section in said bore is adjacent said corresponding groove.

10. The prosthesis according to claim 9 wherein said bore is stopped in one of said condyle parts and said threaded section and said corresponding groove lie in the other of said condyle parts.

11. The prosthesis according to claim 10 wherein said shaft further comprises a post on a medial end thereof for insertion into said condyle part having said stopped bore.

12. The prosthesis according to claim 11 wherein said shaft further comprises wrench engaging means on a lateral end thereof.

13. An implantable prosthesis comprising a first part for affixation to a first bone of a patient, a second part for affixation to a second bone of a patient, and a hinge apparatus connecting said first and second parts, said apparatus comprising a bore in at least one of said first or second parts, said bore being at least partially threaded, and a shaft of biologically compatible material adapted to be secured in said bore, said shaft having a threaded section on said shaft, adapted to threadingly engage said threaded bore, a circumferential groove on said shaft, a corresponding groove in said bore, which corresponding groove will lie adjacent said groove on said shaft when said shaft is properly inserted in said bore, a split ring carried in one of said grooves, said ring being capable of being displaced substantially entirely within said one of said grooves but normally extending radially out of said one of said grooves, said ring having two opposed chamfers, said chamfers being normally exposed out of said one of said grooves, whereby said split ring is displaced within said one of said grooves as said shaft is inserted into said bore until the other of said grooves is adjacent said one of said grooves and whereby said split ring is also displaced within said one of said grooves to withdraw said shaft from said bore.

14. The prosthesis according to claim 13 wherein the threaded portion on said shaft is adjacent said circumferential groove and wherein said threaded section in said bore is adjacent said corresponding groove.

15. The prosthesis according to claim 13 wherein said split ring is carried in said circumferential groove, said ring being capable of being compressibly received substantially entirely within said circumferential groove but normally extending radially outwardly from said circumferential groove.

16. The prosthesis according to claim 15 wherein the threaded portion on said shaft is adjacent said circumferential groove and wherein said threaded section in said bore is adjacent said corresponding groove.

* * * * *